United States Patent
Birmingham et al.

(10) Patent No.: US 8,940,287 B2
(45) Date of Patent: Jan. 27, 2015

(54) METHOD AND COMPOSITION FOR ATTRACTING FRUIT FLIES TO TRAPS

(75) Inventors: Anna L. Birmingham, Vancouver (CA); Iisak S. Andreller, Vancouver (CA); Ervin Kovacs, Vancouver (CA); Jean Pierre Lafontaine, Ladner (CA); Norman Avelino, Richmond (CA); Gerhard Gries, Coquitlam (CA); Alan L. Vaudry, Victoria (CA); John H. Borden, Burnaby (CA)

(73) Assignee: Contech Enterprises Inc., Delta (CA)

( * ) Notice: Subject to any disclaimer, the term of this patent is extended or adjusted under 35 U.S.C. 154(b) by 1452 days.

(21) Appl. No.: 12/019,097

(22) Filed: Jan. 24, 2008

(65) Prior Publication Data
US 2008/0181863 A1    Jul. 31, 2008

Related U.S. Application Data

(60) Provisional application No. 60/886,850, filed on Jan. 26, 2007.

(51) Int. Cl.
| A01N 25/00 | (2006.01) |
| A01M 1/10 | (2006.01) |
| A01M 1/16 | (2006.01) |
| A01N 65/00 | (2009.01) |

(52) U.S. Cl.
CPC ..................................... *A01N 65/00* (2013.01)
USPC .................................... 424/84; 426/1; 43/115

(58) Field of Classification Search
None
See application file for complete search history.

(56) References Cited

U.S. PATENT DOCUMENTS

| 2,979,856 | A | * | 4/1961 | Ponting ........................ 43/132.1 |
| 3,846,557 | A | * | 11/1974 | Mulla et al. ........................ 426/1 |
| 4,160,824 | A | * | 7/1979 | Inazuka et al. .................. 424/84 |
| 4,794,724 | A | * | 1/1989 | Peters ............................. 43/122 |
| 4,849,216 | A | | 7/1989 | Andersen |
| 4,983,390 | A | * | 1/1991 | Levy ............................. 424/404 |
| 5,490,349 | A | | 2/1996 | Muramatsu |
| 6,106,821 | A | | 8/2000 | Baker |
| 6,516,559 | B1 | | 2/2003 | Simchoni et al. |
| 6,543,181 | B1 | | 4/2003 | Baker et al. |
| 6,585,991 | B1 | | 7/2003 | Rojas et al. |
| 6,773,727 | B1 | | 8/2004 | Rojas et al. |
| 2005/0019361 | A1 | * | 1/2005 | Durand et al. ................. 424/405 |

FOREIGN PATENT DOCUMENTS

| CA | 1125509 | | 6/1982 |
| DE | 4424500 | A1 * | 1/1996 |
| WO | 8501638 | A | 4/1985 |

OTHER PUBLICATIONS

Bownes et al., Dietary components modulate yolk protein gene transcription in *Drosophila melanogaster*, Development (1988), vol. 103, pp. 119-128.*
Salek et al., Trehalose—stabilisation of osomphilicity and viability of baker's and distiller's yeast: Applications to storage and drying, Chem. Mikrobiol. Technol. Lebensm., (1995), vol. 17, No. 1/2, pp. 14-21.*
"Molasses Definition and Information", About.com Food Reference (2014), pp. 1-2.*
"Whey", Wikipedia (2014), pp. 1-4.*
American Heritage Dictionary of the English Language. 2003. 4th Ed. 2000, updated 2003. Houghton Mifflin, Boston.
Barrows, W.M., The Reaction of the Pomace Fly, *Drosophila Ampelophila* Loew, to Odorous Substances, J. Exp. Zool., 1907, 4: 515-540.
Hoffmann, A. A., Interspecific Variation in the Response of *Drosophila* to Chemicals and Fruit Odors in a Wind Tunnel, Aust. J. Zool., 1985, 33: 451-460.
Hunter, S.H., et al., Chemicals Attracting *Drosophila*, Am. Nat., 1937, 71: 575-581.
Mallis, A., Handbook of Pest Control (5th Ed.), 1969, Mac Nair-Dorland Co., NY, 1,158 pp.
Ostergaard, S., L., et al., In Vivo Dynamics of Galactose Metabolism in *Saccharomyces cervisiae*: Metabolic Fluxes and Metabolite Levels, Biotechnol. Bioeng., 2001, 73: 412-425.
Phaff, H.J., et al., Yeasts Found in the Alimentary Canal of *Drosophila*, Ecology, 1956, 37: 533-538.
Reed, M.R.., The Olfactory Reactions of *Drosophila melanogaster* Meigen to the Products of Fermenting Bananas, Physiol. Zool., 1938, 11: 317-325.
Spencer, W.P., The *Drosophila* of Jackson Hole, Wyoming—a Taxonomic and Ecological Survey, Am. Midland Nat., 1950, 43: 79-87.
West, A.S., Chemical Attraction for Adult *Drosophila* Species, J. Econ. Entomol., 1961, 54: 677-681.
Zhu, J., et al., Identification of Odors from Overripe Mango that Attract Vinegar Flies, *Drosophila melanogaster*. J. Chem. Ecol., 2003, 29: 899-909.
Doyle, David. "Culturing Flightless Fruit Flies (*Drosophilia melanogaster* & *Drosophila hydei*)", Jan. 30, 2001. Accessed Mar. 25, 2013. <http://www.doylesdartden.com/fruitfly.html>.

* cited by examiner

*Primary Examiner* — Abigail Fisher
*Assistant Examiner* — Frank Choi
(74) *Attorney, Agent, or Firm* — Oyen Wiggs Green & Mutala LLP

(57) ABSTRACT

This invention relates to a novel method of attracting and trapping *Drosophila* species and a composition therefor. A method of attracting flies in the family Drosophilidae which comprises preparing an attractant which is a combination of a moistening agent, yeast and dried and powdered vegetable matter host substrate, including (but not limited to) banana, apple, pear, papaya, mango, orange, tomato, or vegetables, including (but not limited to) potato and squash, and placing this attractive lure in a trap.

16 Claims, No Drawings

METHOD AND COMPOSITION FOR ATTRACTING FRUIT FLIES TO TRAPS

FIELD OF THE INVENTION

This invention relates to a novel method of attracting and trapping *Drosophila* species and a composition therefor.

BACKGROUND OF THE INVENTION

Fruit flies in the Family Drosophilidae are pests in dwellings and commercial premises, wherever fruit or other vegetable matter is left exposed (Mallis 1969). In addition, fruit flies inhabit diverse natural habitats, and are the subject of considerable ecological study. Accordingly, there has been much effort directed to trapping fruit flies, either to control a pest problem or to capture subjects for research.

Fruit flies are strongly attracted to rotting fruit, in which microbial action results in the production of acetic acid. Thus ubiquitous household pests like *Drosophila melanogaster* have earned the common name vinegar flies (Mallis 1969). The association of fruit flies with yeasts is well known, and specific species of yeasts are found in the diet and alimentary canal of various *Drosophila* species (Phaff et al. 1956). Baits comprised of banana mash fermented by bakers' yeast have been used to attract fruit flies since the 1930's (Reed 1938; Spencer 1950; Phaff et al. 1956).

Considerable research has been directed at discovering the natural volatiles that attract fruit flies to their hosts, and incorporating them into lures for commercial traps. Early research disclosed the following attractants: ethanol, acetic acid, ethyl acetate and acetaldehyde (Barrows 1907; Hunter et al. 1937; West 1961). Building on this base, Zhu et al. (2003) found that overripe mango fruit produced several fruit fly attractive compounds, including: ethanol, acetic acid, amyl acetate, 2-phenylethanol and phenylethyl acetate. In cage bioassays, a synergistic 1:22:5 blend of ethanol, acetic acid and 2-phenylethanol attracted six times more *D. melanogaster* than any of the components alone. However, in a field test in a grocery store, traps baited with the three-component blend captured only 30% of the available fruit flies over a five day period. Proceeding further, Baker et al. (2003) teach that effective attraction of *D. melanogaster* can be obtained with compositions that can comprise: a volatile short-chain carboxylic acid (e.g. acetic acid), a volatile short-chain alcohol (e.g. ethanol), a volatile aryl-substituted alcohol (e.g. 2-phenylethanol), a nitrogen compound (e.g. indole or trimethylamine), a sugar (e.g. sucrose), a terpene compound (e.g. α-copaene), ethyl acetate, 2-phenylethylacetate and water.

One problem in using synthetic volatile compositions is that they do not mimic natural circumstances because they do not release carbon dioxide, which is a product of the metabolic action of yeast on a fermentable substrate in the presence of water (Simchoni and Shinitsky 2003). Using a more natural lure composed of fruit and yeast leads to another problem, however, because the rapid degradation of the fruit leads to an unpleasant rotten state. In addition, fruit flies can reproduce in a fruit lure, and the larvae (maggots) will exacerbate the unpleasantness in the eyes of many users.

The inventors herein reasoned that a novel solution to both of the above problems would be to use a dry fruit and yeast mixture, possibly in the form of a powder, which could be stored indefinitely prior to use. To activate the yeast, water could be added just before the lure was placed in a trap.

Water is a necessary component of certain toxic insect feeding baits, which do not include microorganisms. A humectant is a substance that promotes retention of moisture (American Heritage Dictionary 2003). Retention and slow release of water to prolong the acceptability of such toxic baits for termites requires the addition of a humectant, e.g. polyacrylamide (Rojas et al. 2003, 2004). We therefore also reasoned that a novel means of prolonging the bioactivity of an attractive lure for fruit flies would be to add a humectant to the powdered fruit and yeast mixture.

Fruits contain mainly the simple six-carbon sugar fructose, which is rapidly metabolized by yeasts. Thus, the longevity of a powdered fruit and yeast lure for fruit flies would also be limited by the availability of fructose, despite the presence of a humectant. Galactose is also a six-carbon sugar that occurs naturally as one of the products of enzymatic digestion of the 12-carbon sugar lactose, commonly called milk sugar. Because the flux through the galactose pathway is about three-fold slower than for fructose (Ostergaard et al. 2001), we reasoned that a second novel means of prolonging the bioactivity of an attractive lure for fruit flies would be to add a source of galactose, e.g. molasses or cheese whey, to the powdered fruit, yeast and humectant mixture.

Traps for fruit flies come in several forms. One recent design comprises an enclosed reservoir, containing a liquid lure and trapping fluid, and an entry port at the base of a funnel in the top of the trap, that is opened by puncturing before the trap is used (Muramatsu 1996). This trap is available commercially as the Natural Catch Plus Fruit Fly Trap (Natural Insect Control, Stevensville, Ontario, Canada). One modification of this design, the 960 Vector Fruit Fly Trap (Whitmire Micro-Gen Research Laboratories, St. Louis, Mo., USA), has holes in the lid, with a peel-off cover that is removed before use. A further modification of this design, the Dead Easy Fruit Fly Trap, involves a bottle containing the lure and trapping fluid, with a pull-out cap that opens an entry port (Dead Easy Pest Control, Victoria, BC, Canada). Other commercial traps involve a jar with a flip-top lid to provide entry for the fruit flies, combined with a lure that floats in water in which the flies are trapped, and a simple sticky band that is placed around a fruit lure on a flat surface (SpringStar LLC, Woodinville, Wash., USA). Do-it-yourself traps usually incorporate the same elements as the commercial traps, i.e. some kind of entry port and a reservoir in which the flies are captured in a "brew" (ABC Riverina, Wagga Wagga, New South Wales, Australia) or simply an enclosed air space. Containment traps of the Peters Trap Design, 1989, have not been used or adapted for catching fruit flies.

The first three reservoir commercial traps are opaque, and it is impossible to observe whether the traps have captured any flies. The SpringStar jar trap has a label that obscures visual observation of captured flies. It is easy to see captured flies on the SpringStar sticky trap, but there is no receptacle for a lure. All traps that use water as a catching medium may not be totally effective, because fruit flies are often light enough to float on the surface, even though detergent may be added to lessen the surface tension. We therefore judged that a further novel composition might comprise said powdered host substrate and yeast lure, with humectant and galactose extender, contained in a modified Peters trap that had the following characteristics: a transparent outer wall, a transverse dual port entry tube with a cut-away opening into the internal chamber (partially or completely severing the transverse tube), and a removable sticky trapping surface to replace the water trapping medium in the original design. Such a trap would have the advantages of: easy visual inspection of captured flies, containment of the lure and trapping surface inside the chamber of the trap, easily replaceable lures and trapping surface so the trap could be re-used, modification of trap size without any substantial design change, and elimination of spillage and build up of foul odour of the water trapping medium.

The foregoing examples of the related art and limitations related thereto are intended to be illustrative and not exclusive. Other limitations of the related art will become apparent to those of skill in the art upon a reading of the specification.

SUMMARY OF THE INVENTION

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The invention is directed to a method of attracting flies in the family Drosophilidae, which comprises preparing an attractant which is a combination of a moistening agent, yeast and dried and powdered vegetable matter host substrate, including (but not limited to) banana, apple, pear, papaya, mango, orange, tomato, or vegetables, including (but not limited to) potato and squash.

The yeast can be bakers' yeast and the moistening agent can be water. A humectant, including (but not limited to) polyacrylamide, agar, xanthan gum, guar gum, carrageenan and methyl cellulose, can be added to the moistening agent, yeast and powdered host substrate mixture to retain and regulate the release of water.

A source of galactose, including (but not limited to) cheese whey and molasses, can be added to the moistening agent, yeast, powdered host substrate and polyacrylamide mixture to regulate and prolong the metabolic activity of the yeast and the accompanying production and release of carbon dioxide and other metabolic products.

The host substrate powder can make up 1-99% wt of the total mixture, the yeast can make up 1-99% wt of the total mixture, the moistening agent can make up 1-99% wt of the total mixture, the humectant can make up 1-99% wt of the total mixture, and the source of galactose can make up 1-99% wt of the total mixture, the total being 100% wt.

The mixture, excluding the moistening agent, can be placed dry in effective amount into a porous bag, either as loose granules or as a compressed pellet. The porous bag containing an effective amount of the granulated or pelletized mixture of yeast, host substrate powder, humectant and source of galactose can be moistened with or dipped in a moistening agent and placed in a trap designed to capture fruit flies.

The fruit flies can include (but are not limited to) *Drosophila melanogaster, D. funebris, D. repleta, D. busckii, D. affinis, D. falleni, D. tripuctata* and *D. hydei*.

The invention is also directed to a composition which in effective amount is attractive to fruit flies in the family Drosophilidae, said composition comprising a moistening agent [including (but not limited to) water], yeast [including (but not limited to) bakers' yeast], powdered host substrate [including (but not limited to) banana, apple, pear, papaya, mango, orange, tomato, potato and squash], a humectant [including (but not limited to) polyacrylamide, agar, xanthan gum, guar gum, carrageenan and methyl cellusose], and a source of galactose [including (but not limited to) cheese whey and molasses].

In the composition, the powdered host substrate can make up 1-99% wt of the total mixture, the yeast can make up 1-99% wt of the total mixture, the moistening agent can make up 1-99% wt of the total mixture, the humectant can make up 1-99% wt of the total mixture, and the source of galactose can make up 1-99% wt of the total mixture, the total being 100% wt.

The composition, excluding the moistening agent, can be placed dry in effective amount into a porous bag, either as loose granules or as a compressed pellet. The composition can be moistened with or dipped in a moistening agent and placed in a trap designed to capture fruit flies.

The trap can be comprised of a transparent cylindrical or globular receptacle with a replaceable air-tight lid, lateral entry ports leading into a transverse tube that spans the diameter of the trap and which has a partial or wholly cut-out portion at the mid point of the tube, allowing fruit flies to enter the large chamber containing the porous bag lure, and an upright sticky card on which fruit flies that enter the trap are captured.

In addition to the exemplary aspects and embodiments described above, further aspects and embodiments will become apparent by reference to the drawings and by study of the following detailed descriptions.

DETAILED DESCRIPTION OF THE INVENTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

All trapping experiments that yielded quantitative data were set up as randomized complete blocks. Because different numbers of fruit flies were tested in each replicate, the data for each replicate were converted to percentages of the total number of flies captured. If necessary, percentages were transformed by arc sin $\sqrt{0.01x}$ to achieve normality, before being subjected to ANOVA, and (when there were more than two means) the Tukey-Kramer HSD test. In all cases $\alpha=0.05$.

Example 1

Evaluation of Peters Trap Design for Capturing Fruit Flies

Mixed sexed adult fruit flies, *Drosophila melanogaster*, were obtained from a colony maintained at the Department of Biological Sciences, Simon Fraser University, Burnaby, B.C. Fruit flies were reared on decaying overripe bananas in screened cages at a constant 24° C. and a photoperiod of 12:12 (L:D). Adults of both sexes were used in all experiments.

Three experiments were conducted.

Experiment 1 compared two types of traps. The first was the commercially available 225 mL SpringStar spice-jar trap, with a flip-top lid that exposed three 5 mm diameter holes as entry ports, water with a dash of detergent in the bottom of the trap to capture flies that entered through the lid, and a polyethylene lure vessel that floated in the water. The second was a miniaturized Peters trap consisting of the same spice jar, with the lid closed, a 5 mm diameter drinking straw cross bridge (with a 5 mm wide cut-out at mid point that allowed flies to enter the interior of the trap) spanning the 5.5 cm diameter of the jar, a slice of orange in the bottom as a lure, and a 4.5×8 cm sticky card (both sides) placed upright in the jar to capture flies that entered the trap. The two types of trap were tested in three groups of four pairs (12 replicates) randomly placed side by side for one hour in each of four corners of a large screened cage containing hundreds of fruit flies. Observations during the one-hour trapping periods indicated that fruit flies could enter and leave the SpringStar trap, but that no flies left the Peters trap once they entered.

Surprisingly, a total of 1,209 fruit flies were captured in the 12 Peters traps in Experiment 1, almost three times the number captured in the SpringStar traps (Table 1). The results do not reveal whether the superiority of the Peters trap resides in the natural fruit lure, the method of entry into the trap, the sticky card capture device, or some combination of factors. Nonetheless, the results do show that the Peters trap design concept can be miniaturized for catching very small insects like fruit flies, and that a sticky card to trap flies that enter an Peters trap can be used to replace the water trapping medium.

Experiment 2 compared the miniaturized Peters trap fitted with an 8 mm diameter drinking straw entry gate against the SpringStar spice-jar trap. Both traps had a banana slice lure and identical 4.5×8 cm sticky card capture devices, so that the only difference between traps was the method of entry. Four pairs of traps (replicates) were tested for one hour on each of two days for a total of eight replicates. The traps in each pair were randomly positioned side by side at the front or rear of a large screened cage as above. Traps of the Peters design captured 108 fruit flies in total, slightly (but not significantly) more than the 92 flies captured in SpringStar traps (Table 1). This result shows that entry of fruit flies into the Peters trap is at least as good as for the SpringStar trap. The slight superiority of the Peters trap may be because of the lack of escapes.

Table 1. Results of Experiments 1-3, showing that traps of the Peters design, fitted with transverse entry tubes with a cut-away portion at mid-point that allows flies to gain entry into the interior of the trap, and also containing a sticky card capture device, compare very favourably with the commercial SpringStar trap, and also showing that increasing the size of the Peters trap will increase the efficacy of the trap.

Unexpectedly, the larger trap captured 2.4 times more fruit flies than the smaller version (Table 1). This result demonstrates that increasing the diameter of the entry gate, the volume of the interior chamber in the trap, or the size of the sticky card capture surface, or some combination of these factors, can greatly increase the numbers of fruit flies captured.

Example 2

Test of Powdered Host Substrate with and without Yeast

*Drosophila melanogaster* were reared in 175 mL plastic bottles containing 10 g of medium comprising: water, agar, cornmeal, bakers' yeast, molasses, 10% p-hydroxy-benzoic acid and methyl 4-hydroxybenzoate in 95% ethanol. The bottles were kept at 29° C. and 60% RH under a 16:8 h light:dark regime. Only flies enclosing within the previous 24 h period were used in an experiment.

Two experiments were conducted, each with replicates of four treatments tested within separate 38×38×38 cm clear plastic cages. Up to four replicates (cages) were completed per day. White cardboard was placed between cages to minimize any chemical or visual interference. Treatments were offered in 40 mL polyethylene vials containing a 2.5×10 cm piece of waxed cardboard treated on one side with Tanglefoot® (Tanglefoot Co., Grand Rapids Mich.) to capture responding insects. Approximately 20 mixed sex adult *D. melanogaster* in a 9.5 cm diameter plastic Petri dish were placed in the middle of the cage floor for 20 min, after which the lid was removed, allowing the flies to respond to the treatment vials for 24 h at 26° C. and a 16:8 L:D regime.

Banana chip powder treatments were prepared from Aloha Brand banana chips (Dole Food Co, Inc., Honolulu, Hi.) which contained deep fried banana slices, coconut oil,

TABLE 1

Results of Experiments 1-3, showing that traps of the Peters design, fitted with transverse entry tubes with a cut-away portion at mid-point that allows flies to gain entry into the interior of the trap, and also containing a sticky card capture device, compare very favourably with the commercial SpringStar trap, and also showing that increasing the size of the Peters trap will increase the efficacy of the trap.

| EXP. NO. | NO. REPLICATES | TREATMENT | TOTAL NO. OF FLIES CAPTURED | MEAN PERCENT OF TOTAL FLIES CAPTURED ± SE[a] |
|---|---|---|---|---|
| 1 | 12 | SpringStar trap | 413 | 22.4 ± 2.0 b |
|   |   | Miniaturized Peters trap | 1,209 | 77.6 ± 2.9 a |
| 2 | 8 | SpringStar trap | 92 | 45.3 ± 8.4 a |
|   |   | Miniaturized Peters trap | 108 | 54.7 ± 8.4 a |
| 3 | 2 | Slim Peters trap (1 L) | 427 | 82.5 ± 8.5 a |
|   |   | Miniaturized Peters trap (225 mL) | 135 | 17.5 ± 8.5 b |

[a]Means within a pair followed by different letters are significantly different, ANOVA, $P < 0.05$.
For Experiments 1-3, repectively: $F = 183.13$, $df = 1$, $P < 0.0001$; $F = 2.06$, $df = 1$, $P = 0.1768$; $F = 29.43$, $df = 1$, $P = 0.0323$.

Experiment 3 compared the miniaturized Peters trap with a larger 21.5×8 cm cylindrical 1 L commercial Peters trap used for trapping other insects. Both traps were baited with banana slice lures. The miniaturized trap had a 4.5×8 cm sticky card and an 8 cm diameter entry gate as in Experiment 2, while the larger trap had a 5×18 cm sticky card capture device. Two replicates were run at different times in a residential apartment, with the traps in each pair randomly placed on a table.

sucrose and/or honey. The chips were crushed into a fine powder, water was added (20 mL per 3 g of powder) and the mixture was stirred into a paste. After 20 min, the paste was added in 8.5 g aliquots to the 40 mL test vials. Banana chip powder with yeast and water was prepared in the same manner as the above treatment, except that 0.05 g of bakers' yeast (Canada Safeway Ltd, Calgary, Alberta) was thoroughly mixed with the chip powder before the water was added.

Mashed banana was made up by mixing 10 mL of water with 5 g of crushed banana. The mashed banana plus yeast treatment was identical to the mashed banana treatment, except that 0.05 g of yeast was added to the 5 g of crushed banana before the water was added. Both banana treatments were also tested as 5 g aliquots in the 40 mL test vials.

Treatments in Experiment 4 (N=12 replicates) included: 1) powdered banana chips plus yeast plus water, 2) mashed banana plus water, 3) mashed banana plus yeast plus water and 4) unbaited control. Test vials were randomly placed in the four corners of each cage. Four replicates were run per day for three days. Treatments in Experiment 5 (N=10 replicates) were the same as in the Experiment 4, except that the unbaited control was replaced with banana chip powder plus water. Test vials were grouped together in random placement in a 2×2 grid in one corner of each cage. After 24 h, the number of flies on each sticky card was counted.

In Experiment 4, traps baited with banana chip powder plus yeast, mashed banana or mashed banana plus yeast all captured significantly more fruit flies than unbaited control traps, but there was no significant difference among the three treatments (Table 2). This experiment demonstrates that powdered banana chips can effectively replace banana as an attractive stimulus for fruit flies.

When the four stimuli in Experiment 5 were placed close together, traps baited with powdered banana chips plus yeast unexpectedly captured significantly more flies than traps baited with any of the other stimuli, over twice as many flies as mashed banana, and over three times as many flies as mashed banana plus yeast or powdered banana chips (Table 3). These results show that when the flies are challenged with a choice of traps at close range, they clearly prefer the yeast plus powdered banana plus water lure over traps baited with a natural fruit lure comprised of mashed banana.

TABLE 2

Results of Experiment 4 (N = 12) showing that powdered banana chips can replace banana as an attractive stimulus.

| TREATMENT | TOTAL NO. OF FLIES CAPTURED | MEAN PERCENT OF TOTAL FLIES CAPTURED ± SE[a] |
|---|---|---|
| Powdered banana chips plus yeast plus water | 61 | 36.9 ± 6.5 a |
| Mashed banana plus yeast plus water | 40 | 22.7 ± 3.6 a |
| Mashed banana plus water | 65 | 32.5 ± 5.6 a |
| Unbaited control | 2 | 1.1 ± 0.7 b |

[a]Means followed by the same letter are not significantly different, Tukey-Kramer HSD test, $P < 0.05$. $F = 22.86$, $df = 3$, $P < 0.0001$.

In spite of the efficacy of the powdered banana chips plus yeast lure in Experiment 5, it would not be practical to require that users mix up a paste to bait a trap for operational or commercial purposes. Moreover, any water-based paste exposed to the air would be expected to dry out within a day, effectively terminating any attraction. Nonetheless, the results show promise for a powdered banana plus yeast lure that could replace the fruit itself, without having to employ an expensive lure based on a blend of synthetic chemicals.

TABLE 3

Results of Experiment 5 (N = 10) showing that, when given a close-range choice, fruit flies are captured in significantly greater numbers in traps baited with powdered banana chips plus yeast plus water than with any other stimulus.

| TREATMENT | TOTAL NO. OF FLIES CAPTURED | MEAN PERCENT OF TOTAL FLIES CAPTURED ± SE[a] |
|---|---|---|
| Powdered banana chips plus yeast plus water | 124 | 47.0 ± 4.4 a |
| Mashed banana plus water | 55 | 24.1 ± 4.5 b |
| Mashed banana plus yeast plus water | 39 | 14.8 ± 3.8 b |
| Powdered banana chips plus water | 41 | 14.1 ± 3.0 b |

[a]Means followed by the same letter are not significantly different, Tukey-Kramer HSD test, $P < 0.05$. Data converted by arc sin $\sqrt{0.01x}$ prior to analysis. $F = 12.01$, $df = 3$, $P < 0.0001$.

Example 3

Formulation of Tea Bag Lures, with and without a Humectant

To ensure the practicality of the lure used in the trap for operational and commercial purposes and to prevent extra work and mess when mixing a paste to bait a trap, teabags were proposed as a receptacle to keep the bait contents together and wet. However, when teabags are exposed to the air they quickly dry out. Furthermore, because the most efficient trap would contain a sticky card to prevent escape, the teabag needed to stay wet yet not affect the adhesive on the sticky card. To avoid drying out the bait and reducing its effectiveness, we decided to add a humectant that could retain water yet not alter the effectiveness of the bait. The inventors' objective was to construct a moist teabag without water leakage. Polyacrylamide gel powder was proposed and in Experiment 6 a series of teabags were constructed containing powdered banana chips, yeast and different weights of the gel powder. Treatment contents were placed in 3.8×6.3 cm teabags (t-sac Brand GmbH, Hannover, Germany). Each teabag contained 1.0, 0.5, 0.1 or 0.05 g polyacrylamide gel powder (Integra Tech Associates, Overland park, Kans.), added to 0.1 g Fleischmann's Traditional Active Dry Yeast (ACH Food Companies Inc., Memphis, Tenn.), and 1.0 g banana chip powder. Banana chip powder treatments were prepared from crushed banana chips (bulk food, Canada Safeway Ltd, Calgary, Alberta) which contained deep fried banana slices, coconut and/or palm oil, sucrose and/or honey.

Teabags were dipped in water for 10 sec, the excess water was allowed to drip off, and the bags were left in the miniaturized Peters traps described in Example 1, Experiment 2, except that the 8 mm diameter drinking straw was replaced by a hard acrylic plastic entry tube (6 mm inside diameter, 9 mm outside diameter), without sticky cards. They were observed daily for four days, then daily for four days after a two day break.

Teabags containing 0.1 to 0.05 g polyacrylamide gel powder had four desirable characteristics. They did not burst after being dipped in water, they soaked up water faster than teabags with 1.0 or 0.5 g of polyacrylamide gel powder, they retained enough water to completely wet the rest of the teabag contents and they stayed wet to the touch longer than the other four weights of teabags. Therefore, 0.05 g polyacrylamide gel powder was selected as the optimal amount.

Example 4

Test of Powdered Dehydrated Banana versus Powdered Banana Chips as a Host Substrate Experiment 7 was conducted to determine if fruit flies, *Drosophila melanogaster*, reared as in Example 1, were more attracted to powdered dehydrated banana than powdered banana chips.

Four groups of four replicates each were run for 24 h in four different time periods, for a total of 16 replicates. Each replicate had two treatments, so that for each time period, eight traps, consisting of four randomly-assigned treatments within each pair, were positioned equidistant around the periphery of the floor of a 133×66×47 cm clear plastic cage. Treatments were offered in the miniaturized Peters trap described in Example 1, Experiment 2, except that the 8 mm diameter drinking straw was replaced by the hard acrylic plastic entry tube described in Example 3, and the sticky cards (Better World Manufacturing Inc., Fresno, Calif.) were 9.2×5.4 cm, and were sticky on one side only.

Treatment contents were placed in 3.8×6.3 cm teabags (t-sac Brand GmbH, Hannover, Germany). Each teabag contained 0.15 g Fleischmann's Traditional Active Dry Yeast (ACH Food Companies Inc., Memphis, Tenn.), 0.05 g polyacrylamide gel powder (Integra Tech Associates, Overland park, Kans.) and 1.5 g of either banana chip powder (Treatment 1) or dehydrated banana powder (Treatment 2).

Banana chip powder treatments were prepared as in Example 3, Experiment 6. Dehydrated banana powder treatments were prepared from freeze dried banana powder (Nature's Flavors, Orange, Calif.) which contained only bananas.

Teabags were dipped in tepid tap water for 10 sec, excess water was allowed to drip off, and the teabag was dropped into a trap. The sticky card was bent in the middle lengthwise, the backing removed and the card was inserted upright into the trap.

A number of mixed sex *Drosophila melanogaster* in a 16 cm diameter covered plastic dish were placed in the middle of the cage floor for 5 min, after which the lid was removed and the flies allowed to respond to the treatment teabags for 24 h at 22° C. The number of fruit flies on each sticky card was then counted.

Traps with teabags containing the dehydrated banana powder teabags caught significantly more fruit flies than traps with teabags containing pulverized banana chips (Table 4). The superiority of the teabags containing banana powder was consistent for each group of four replicates. This experiment demonstrates that dehydrated banana powder is an effective replacement for crushed banana chips when used as a lure for fruit flies.

TABLE 4

Results of Experiment 7 (N = 16), demonstrating that traps baited with teabags containing dehydrated banana powder teabags caught more fruit flies than traps baited with teabags containing banana chip powder.

| TREATMENT | TOTAL NO. OF FLIES CAPTURED | MEAN PERCENT OF TOTAL FLIES CAPTURED ± SE[a] |
|---|---|---|
| Teabag with banana chip powder | 21 | 25.8 ± 7.4 b |
| Teabag with banana powder | 73 | 61.7 ± 9.2 a |

[a]Means followed by different letters are significantly different, ANOVA, F = 8.32, df = 1, P = 0.0081. Data transformed by arc sin $\sqrt{0.01x}$ prior to analysis.

Example 5

Selection of Carrageenan Gel Powder as an Alternative Humectant to Polyacrylamide Gel Powder Because the polyacrylamide gel powder eventually breaks down into its carcinogenic monomer constituents, we decided to determine whether it could be replaced by an alternative humectant. Four food-grade humectants were tested in Experiment 8: agar, carrageenan gum, guar gum and xanthan gum. Teabags were constructed as in Example 4, using only the dehydrated banana powder and 0.2 g of agar powder (Westpoint Distributors Ltd., Vancouver, B.C.), carrageenan gum powder (Genugel® carrageenan type CI-102, CP Kelco U.S. Inc., Chicago, Ill.), guar gum powder (bulk food, Famous Foods, Vancouver, B.C.) or xanthan gum powder (Kelzan® S, CP Kelco U.S. Inc., Chicago, Ill.). These teabags were dipped in water for 10 sec, the excess water was allowed to drip off, and the bags were left in open air. They were observed daily for three days, and after five days.

Teabags containing carrageenan gum gel powder had three desirable characteristics. They had no residual odour, they did not swell up after being dipped in water, and they stayed wet to the touch longer than the other three types of teabags. Therefore, carrageenan gum gel was selected as an alternative to polyacrylamide gel powder, and was used in all subsequent experiments.

Example 6

Test of Powdered Dehydrated Banana Teabags Versus a Slice of Banana

Experiment 9 was conducted to determine if fruit flies, *Drosophila melanogaster*, reared as in Example 1, were more attracted to powdered dehydrated banana than a slice of banana.

Four groups of four replicates each were run in the miniaturized Peters trap as described in Example 4. For the first treatment, teabags contents included 2.0 g of freeze dried banana powder (Nature's Flavors, Orange, Calif.), 0.2 g of Fleischmann's Traditional Active Dry Yeast (ACH food Companies Inc., Memphis, Tenn.) and 0.2 g of carrageenan gum powder (Genugel® carrageenan type CI-102, CP Kelco U.S. Inc., Chicago, Ill.). For the second treatment, banana slices were cut from bananas obtained at the local grocery and cut into 2.0 g pieces.

For each replicate, teabags were dipped in tepid tap water for 10 sec, excess water was allowed to drip off, and the teabag was dropped into a trap. Cut slices of banana were dropped into the other trap. The sticky card for each trap was bent in the middle lengthwise, the backing removed and the card was inserted upright into the trap.

A number of mixed sex *Drosophila melanogaster* in a 16 cm diameter covered plastic dish were placed in the middle of the cage floor for 5 min, after which the lid was removed and the flies allowed to respond to the baited traps for 24 h at 22° C. The number of fruit flies on each sticky card was then counted.

Unexpectedly, traps with teabags containing the dehydrated banana powder caught 62.4% of all flies captured, significantly more than traps baited with a slice of banana (Table 5). This experiment demonstrates that dehydrated banana powder is a superior replacement for a slice of banana when used as a lure for fruit flies.

TABLE 5

Results of Experiment 8 (N = 16), demonstrating that traps baited with teabags containing dehydrated banana powder teabags caught more fruit flies than traps baited with a slice of banana.

| TREATMENT | TOTAL NO. OF FLIES CAPTURED | MEAN PERCENT OF TOTAL FLIES CAPTURED ± SE[a] |
|---|---|---|
| Trap with banana powder teabag | 206 | 62.4 ± 6.6 a |
| Trap with banana slice | 150 | 37.6 ± 6.6 b |

[a]Means followed by different letters are significantly different, ANOVA, F = 15.17, df = 1, P = 0.0007.

Example 7

Effect of Re-Wetting on Bioactivity of Teabag Lures

Experiment 10 was conducted to determine if fruit flies, *Drosophila melanogaster*, reared as in Example 1, were attracted to aged and re-wetted powdered dehydrated banana teabags.

Four replicates were run in miniaturized Peters traps as described in Example 4. Teabags were prepared as described in Example 6. Treatments included teabags that were either wet 48 h previously, wet 48 h previously and then re-wet immediately before the experiment, and freshly wet teabags.

All teabags were prepared by dipping in tepid tap water for 10 sec, allowing excess water to drip off, and dropping the teabag into a trap. Sticky cards were bent in the middle lengthwise, the backing removed and the cards inserted upright into the traps.

A number of mixed sex *Drosophila melanogaster* in a 16 cm diameter covered plastic dish were placed in the middle of the cage floor for 5 min, after which the lid was removed and the flies allowed to respond to the baited traps for 24 h at 22° C. The number of fruit flies on each sticky card was then counted.

TABLE 6

Results of Experiment 10 (N = 4), demonstrating that traps baited with aged teabags caught more fruit flies than traps baited with freshly wet teabags.

| TREATMENT | TOTAL NO. OF FLIES CAPTURED | MEAN PERCENT OF TOTAL FLIES CAPTURED ± SE[a] |
|---|---|---|
| Wet teabag 48 h previously | 29 | 45.0 ± 3.4 a |
| Wet teabag 48 h previously then re-wet | 27 | 39.0 ± 2.5 a |
| Freshly wetted teabag | 12 | 16.0 ± 2.5 a |

[a]Means followed by the same letter are not significantly different, Tukey-Kramer HSD test, P ≤ 0.05. F = 28.94, df = 2, P = 0.0001.

Unpredictably, regardless of re-wetting, teabags that had been wet 48 h previously caught more than double the number of fruit flies than freshly wetted teabags. This experiment demonstrates that banana powder teabags with carrageenan gel powder as a humectant increase in potency over the first 48 h after wetting, and continue to attract and capture fruit flies for at least three days. The results also demonstrate that at least for three days duration, re-wetting is not necessary.

Example 8

Emission of $CO_2$ from Teabags with and without Cheese Whey

When all components of the teabag are considered, the limiting factor for longevity of attractiveness may be the rapidity with which the yeast uses up the available substrate, resulting in a decrease in $CO_2$ production. The $CO_2$ generated from yeast is a fruit fly attractant and adding a source of galactose to increase the longevity of $CO_2$ production by the yeast may prolong the attractiveness of a teabag lure. Experiment 11 was conducted to determine how long gas, assumed to be $CO_2$, was generated from dehydrated banana powder teabags, with and without cheese whey as a source of galactose.

An apparatus to observe the generation of $CO_2$ was constructed. Paired cylindrical 225 mL plastic jars were each closed with an airtight rubber stopper, through which a plastic tube was inserted. The plastic tube was attached to a glass pipette with the thin end of the pipette submerged in water in a glass test tube. The water was dyed green to aid in observation. This set up allowed for observation of gas escaping from the trap and bubbling into the green water.

Teabags were constructed as described in Example 4. Teabags with cheese whey were loaded as above, with the addition of 0.5 g powdered cheese whey (bulk food product, Famous Foods, Vancouver, B.C.). Teabags were dipped in tepid tap water for 10 sec, excess water was allowed to drip off, and each teabag was dropped separately into one of the plastic jars. Rates of escaping gas were determined by counting bubbles released through the dyed water for 10 min observation periods as indicated in Table 7.

Unexpectedly, Experiment 11 demonstrated that addition of cheese whey to the teabag more than doubled the duration that the yeast produced a gas presumed to be $CO_2$ (Table 7).

TABLE 7

Timed observations of bubbles of gas escaping from the observation apparatus, demonstrating that the addition of cheese whey to banana powder, yeast, polyacrylamide and water in a teabag increased the duration of gas production by yeast.

| Time after start of experiment | BUBBLES PER 10 MIN OBSERVATION PERIOD | |
|---|---|---|
| | With cheese whey | Without cheese whey |
| 10 min | 3 | 6 |
| 1 h | 2 | 1 |
| 2 h | 2 | 1 |
| 3 h | 1 | 0 |
| 4 h | 2 | 1 |
| 22 h | 1 | 1 |
| 23 h | 1 | 0 |
| 24 h | 1 | 0 |
| 26 h | 1 | 0 |
| 42 h | 1 | 0 |
| 43 h | 1 | 0 |
| 44 h | 1 | 0 |
| 45 h | 1 | 0 |
| 47 h | 0 | 0 |
| 72 h | 0 | 0 |
| 73 h | 0 | 0 |
| 74 h | 0 | 0 |
| 75 h | 0 | 0 |

Example 9

Comparative Performance of Miniaturized Peters Trap Versus Commercially-Available Traps Experiment 12 was conducted to determine if the miniaturized Peters trap was commercially competitive.

Twelve replicates were run comparing the number of fruit flies caught in miniaturized Peters traps as described in Example 4, versus three commercially-available traps: the Deadeasy Fruit Fly Trap (Dead Easy Pest Control, Victoria, B.C), the 960 Vector Fruit Fly Trap (Whitmire Micro-Gen Research Laboratories, Inc., St. Louis, Mo.), and, Natural Catch Fruit Fly Trap (Bio-Logic, Inc., Milwaukee, Oreg.). Teabags were prepared as described in Example 6. Each treatment included one trap of each type set up according to the instructions on the label.

Teabag lures were prepared as in Example 6. They were dipped in tepid tap water for 10 sec, excess water was allowed to drip off, and they were dropped into a miniaturized trap. Sticky cards were bent in the middle lengthwise, the backing removed and the cards inserted upright into the traps.

A 16 cm diameter covered plastic dish containing mixed sex *Drosophila melanogaster* was placed in the middle of the bioassay cage floor for 5 min, after which the lid was removed and the flies were allowed to respond to the baited traps for 24 h at 22° C. The number of fruit flies on each sticky card (miniaturized Peters traps) or in the liquid trapping medium (commercially-available traps) was then counted.

Surprisingly, the miniaturized Peters traps baited with teabag lures containing freeze dried banana powder, bakers' yeast and a humectant caught significantly more fruit flies than any other trap tested (Table 9). This result demonstrates clearly that the miniaturized Peters trap with the new teabag lure is more effective at catching fruit flies, *Drosophila melanogaster*, than three widely-available commercial traps.

TABLE 9

Results of Experiment 12 (N = 12), demonstrating that miniaturized Peters traps with a banana powder, yeast and humectant teabag lure captured significantly more fruit flies than three common commercially-available traps.

| TRAP TYPE | TOTAL NUMBER OF FLIES CAPTURED | MEAN PERCENT OF TOTAL FLIES CAPTURED ± SE[a] |
|---|---|---|
| Pherotech | 456 | 70.5 ± 5.7 a |
| 960 Vector | 152 | 23.5 ± 5.2 b |
| Dead Easy | 23 | 3.6 ± 1.2 c |
| Natural Catch | 17 | 2.5 ± 1.0 c |

[a]Means followed by the same letter are not significantly different, Tukey-Kramer HSD test, F = 58.5537, df = 3.44, P < 0.001

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

REFERENCES

US Patent Documents

Baker, T. C., J. Zhu and K.-C. Chung. 2003. Fruit fly attractant compositions. U.S. Pat. No. 6,543,181.
Muramatsu, S. 1996. Insect trap with liquid attractant. U.S. Pat. No. 5,490,349.
Rojas, G. M., J. A. Morales-Ramos and E. G. King. 2003. Termite bait matrix. U.S. Pat. No. 6,585,991.
Rojas, M. G., J. A. Morales-Ramos and P. J. Wan. 2004. Use of gossypol and related terpenes for control of urban and agricultural pests. U.S. Pat. No. 6,773,727.
Simchoni, M. and M. Shinitsky. 2003. Insect trap. U.S. Pat. No. 6,516,559.

Other Publications

American Heritage Dictionary of the English Language. 2003. 4th Ed. 2000, updated 2003. Houghton Mifflin, Boston.
Barrows, W. M. 1907. Reaction of pomace fly to odorous substances. J. Exp. Zool. 4: 515-540.
Hoffmann, A. A. 1985. Interspecific variation in the response of *Drosophila* to chemicals and fruits odors in a wind tunnel. Aust. J. Zool. 33: 451-460.
Hunter, S. H., H. M. Kaplan and E. V. Enxmann. 1937. Chemicals attracting *Drosophila*. Am. Nat. 71: 575-581.
Mallis, A. 1969. Handbook of pest control (5th Ed.). Mac Nair-Dorland Co., NY. 1,158 pp.
Ostergaard, S., L. Olsson and J. Nielsen. 2001. In vivo dynamics of galactose metabolism in *Saccharomyces cervisiae*: metabolic fluxes and metabolite levels. Biotechnol. Bioeng. 73: 412-425.
Phaff, H. J., M. W. Miller, J. A. Recca, M. Shifrine and E. M. Mrak. 1956. Yeasts found in the alimentary canal of *Drosophila*. Ecology 37: 533-538.
Reed, M. R. 1938. The olfactory reactions of *Drosophila melanogaster* Meigen to the products of fermenting bananas. Physiol. Zool. 11: 317-325.
Spencer, W. P. 1950. The *Drosophila* of Jackson Hole, Wy.—a taxonomic and ecological survey. Am. Midland Nat. 43: 79-87.
West, A. S. 1961. Chemical attraction for adult *Drosophila* species. J. Econ. Entomol. 54: 677-681.
Zhu, J., K.-C. Park and T. C. Baker. 2003. Identification of odors from overripe mango that attract vinegar flies, *Drosophila melanogaster*. J. Chem. Ecol. 29: 899-909.

What is claimed is:

1. A composition for attracting flies in the family Drosophilidae comprising
    dried, powdered and unfermented fruit or vegetable matter,
    a humectant; and
    live yeast,
    wherein the composition is dry and activatable by contact with a moistening agent.

2. A composition according to claim 1 wherein the dried, powdered and unfermented fruit or vegetable matter is selected from the group consisting of dried, powdered and unfermented banana, apple, pear, papaya, mango, orange, tomato, potato and squash.

3. A composition according to claim 1 wherein the live yeast comprises bakers' yeast.

4. A composition according to claim 1 where the humectant is selected from the group consisting of polyacrylamide, agar, xanthan gum, guar gum, carrageenan, and methyl cellulose.

5. A composition according to claim 1 further comprising a source of galactose.

6. A composition according to claim 1 wherein the dried, powdered and unfermented fruit or vegetable matter makes up 1-98% wt of the total composition, the yeast makes up 1-98% wt of the total composition, and the humectant makes up 1-98% wt of the total composition.

7. A composition according to claim 5 wherein the dried, powdered and unfermented fruit or vegetable matter makes up 1-97% wt of the total composition, the yeast makes up 1-97% wt of the total composition, the humectant makes up 1-97% wt of the total composition, and the source of galactose makes up 1-97% wt of the total composition, the total being 100% wt.

8. A method of attracting flies in the family Drosophilidae comprising:
    (a) providing the composition of claim 1; and
    (b) activating the composition prior to use by contacting the composition with a moistening agent.

9. A method according to claim 8 wherein the moistening agent comprises water.

10. A method according to claim 8 wherein the dried, powdered and unfermented fruit or vegetable matter is selected from the group consisting of dried powdered and unfermented banana, apple, pear, papaya, mango, orange, tomato, potato and squash.

11. A method according to claim 8 wherein the live yeast comprises bakers' yeast.

12. A method according to claim 8 where the humectant is selected from the group consisting of polyacrylamide, agar, xanthan gum, guar gum, carrageenan, and methyl cellulose.

13. A method according to claim 8 further comprising a source of galactose.

14. A method according to claim 8 wherein the dried, powdered and unfermented fruit or vegetable matter makes up 1-98% wt of the total composition, the yeast makes up 1-98% wt of the total composition, and the humectant makes up 1-98% wt of the total composition.

15. A method according to claim 8 wherein step (a) further comprises placing the composition into a water-porous bag.

16. A method according to claim 15 wherein step (a) further comprises placing the water-porous bag containing the composition into a trap comprising:
- a transparent cylindrical or globular receptacle;
- a removable air-tight lid;
- lateral entry ports;
- a transverse tube that spans a diameter of the trap and comprises a partially or wholly cut-out portion at a mid point of the tube to allow fruit flies to enter the receptacle containing the water-porous bag, the lateral entry ports connected to the tube; and an upright sticky card on which flies that enter the trap are captured.

* * * * *